United States Patent [19]
Singh

[11] Patent Number: 5,912,019
[45] Date of Patent: Jun. 15, 1999

[54] COMPOUNDS FOR REDUCING ISCHEMIA/ REPERFUSION INJURY

[75] Inventor: Inderjit Singh, Mount Pleasant, S.C.

[73] Assignee: MUSC Foundation for Research Development, Charleston, S.C.

[21] Appl. No.: 08/951,262

[22] Filed: Oct. 16, 1997

Related U.S. Application Data

[60] Provisional application No. 60/037,693, Feb. 7, 1997.

[51] Int. Cl.$^6$ .................. A61K 33/26; A61K 31/675; A61K 31/35; A61K 31/195
[52] U.S. Cl. ..................... 424/608; 514/80; 514/460; 514/562; 514/563
[58] Field of Search ................. 424/608; 514/80, 514/460, 562, 563

[56] References Cited

U.S. PATENT DOCUMENTS

| | | |
|---|---|---|
| 4,724,239 | 2/1988 | Morgan . |
| 5,084,482 | 1/1992 | Hirsch et al. . |
| 5,221,537 | 6/1993 | Hecht et al. . |
| 5,498,427 | 3/1996 | Menasche . |

FOREIGN PATENT DOCUMENTS

WO 88/05044  7/1988  WIPO .

OTHER PUBLICATIONS

Koeppel et al, Chemical Abstracts, vol. 125, abstract No. 158140, 1996.

Sochman et al, Biological Abstracts, vol. 96, abstract No. 128371, 1996.

Vivot et al, Chemical Abstracts, vol. 119, abstract No. 20465, 1993.

Osborne et al, Chemical Abstracts, vol. 110, abstract No. 128422, 1989.

Zhang et al, Chemical Abstracts, vol. 121, abstract No. 55109, 1994.

Ichikawa, Chemical Abstracts, vol. 120, abstract No. 267250, 1994.

Vermulapalli et al, Chemical Abstracts, vol. 119, abstract No. 108719, 1993.

Bird et al, Chemical Abstracts, vol. 122, abstract No. 96132, 1995.

*Primary Examiner*—William R. A. Jarvis
*Attorney, Agent, or Firm*—Needle & Rosenberg, P.C.

[57] ABSTRACT

Disclosed herein are compositions containing NO donors, inhibitors of iNOS induction, and endopeptidase inhibitors, and methods for their use for combating injury induced by ischemia and reperfusion following ischemic episodes.

19 Claims, 6 Drawing Sheets

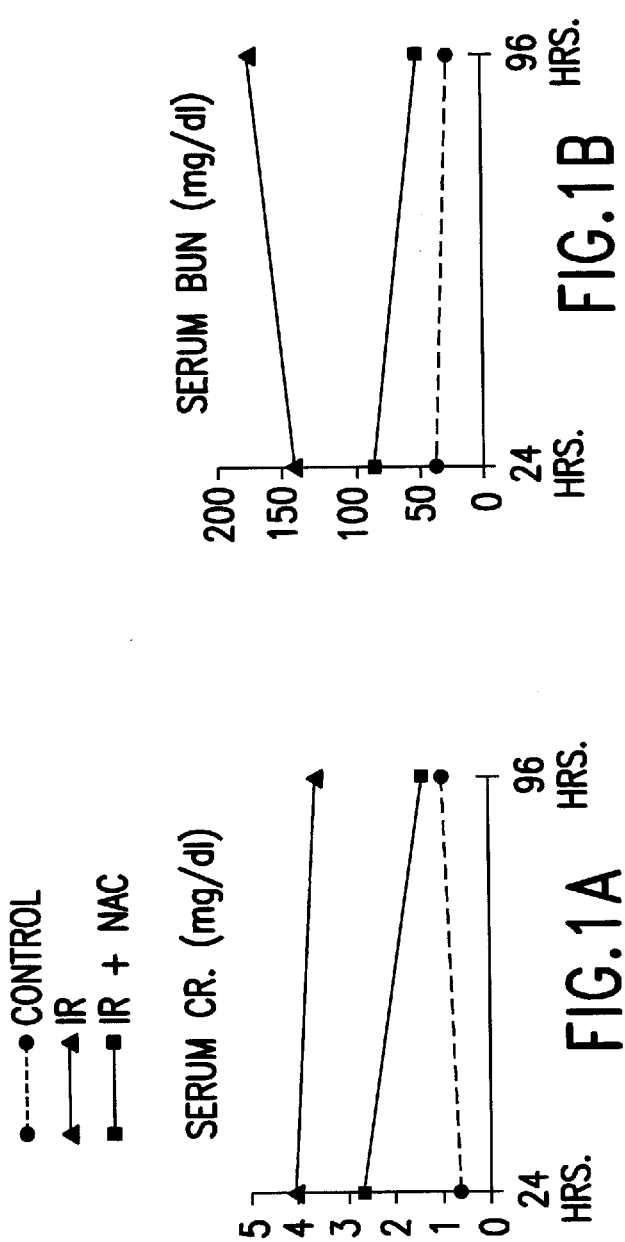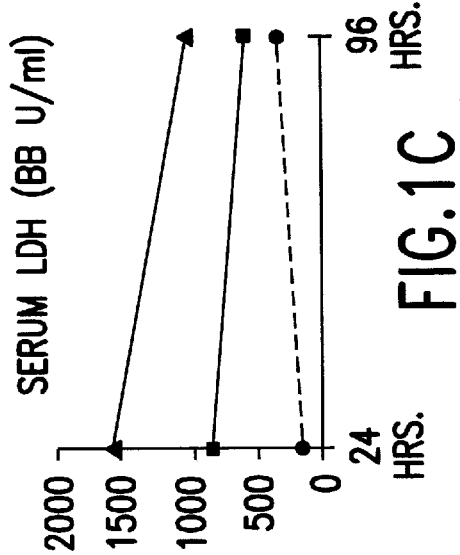

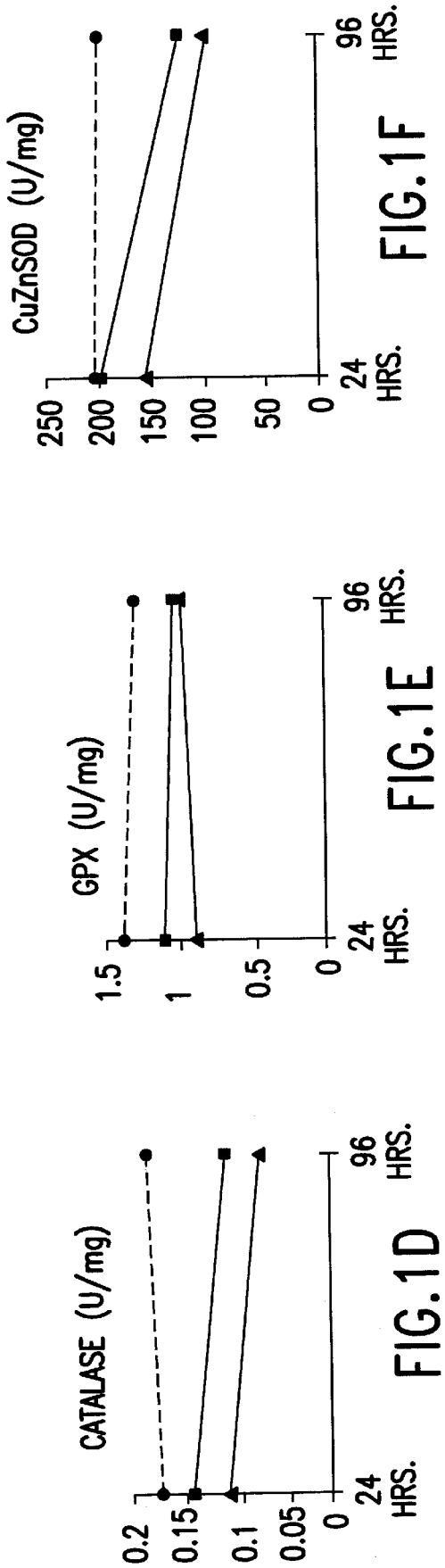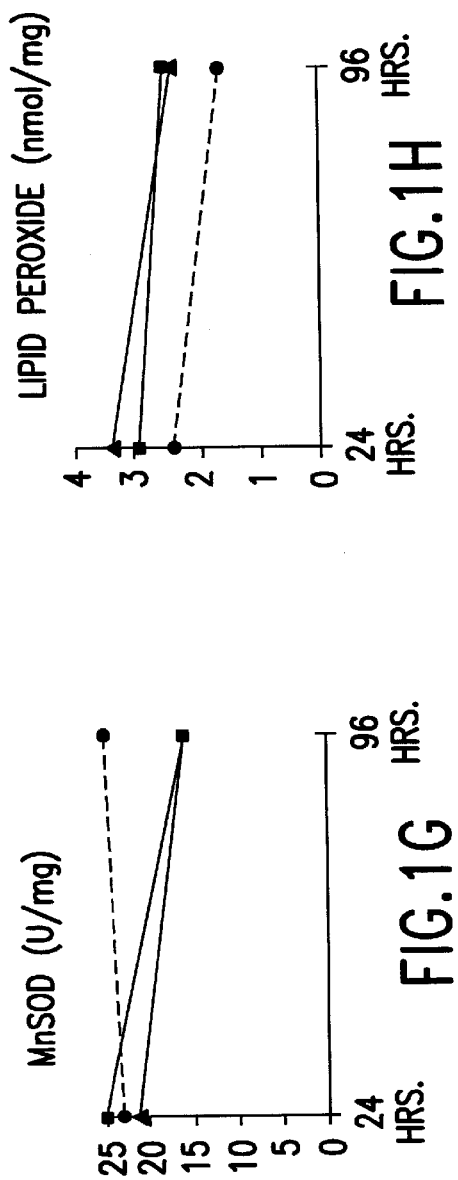

COMPOUNDS FOR REDUCING ISCHEMIA/REPERFUSION INJURY

RELATED APPLICATIONS

This application claims priority under 35 U.S.C. 119(e) to provisional application No. 60/037,693, filed Feb. 7, 1997.

BACKGROUND OF THE INVENTION

1. Field of the Invention

The present invention relates to compositions for and methods of reducing and eliminating injuries to organs and skeletal tissues subjected to ischemic episodes. The invention also relates to organ transplants, and to preconditioning and preservation of organ transplants. The invention relates particularly to compositions useful for limiting free radical injury to such organs and tissues from ischemic episodes.

2. Background Art

Ischemic insult, i.e., the localized deficiency of oxygen to an organ or skeletal tissue, is a common and important problem in many clinical conditions. The problem is especially acute in organ transplant operations in which a harvested organ is removed from a body, isolated from a blood source, and thereby deprived of oxygen and nutrients for an extended period of time. Ischemic insult also occurs in certain clinical conditions such as sickle cell anemia and septic shock which may result from hypotension or organ disfunction. Depending on the duration of the insult, the ischemia can disturb cellular metabolism and ion gradients, and ultimately cause irreversible cellular injury and death.

Reactive oxygen species are natural but undesirable byproducts of cellular metabolic processes in different subcellular compartments and membranes. These radicals are highly reactive and destructive to cell tissue because of the presence of unpaired electrons. These free radical reactive oxygen species include, for example, $O_2^-$, $OH^-$, $H_2O_2$, NO, and $ONOO^-$. In normal systems, injury from these reactive species is prevented or minimized by radical scavenging systems, including enzymatic systems such as catalase, CuZn-superoxide dismutase, Mn-superoxide dismutase, and glutathione peroxidase. Non-enzymatic radical scavenging systems are also present in metabolic processes, such as glutathione, vitamin E, and carotene.

Reactive oxygen species reportedly are formed at a greater rate than they can be scavenged by natural radical scavenging systems when blood is reperfused to an area previously exposed to ischemia. The ischemia/reperfusion also has been reported to cause down regulation of antioxidant enzymatic defenses. As a result of these reports, researchers have incriminated reactive oxygen species as a principal component of the pathology which causes cellular injury as a result of ischemic insult.

The events that cause reactive oxygen species to be produced faster than they can be scavenged by radical scavenging systems following an ischemic episode are not well-understood. The damage caused by these reactive oxygen species has, however, been well documented, and includes increases in intracellular calcium, lipolysis, production of free fatty acids and bioactive arachidonic acid metabolites, proteolysis and decreases in levels of cellular phospholipids.

Ischemia is also associated with various clinical conditions, such as septic shock, that do not involve discreet reperfusive episodes. Septic shock as a result of hypotension and organ dysfunction in response to infectious sepsis is one of the major causes of death. The manifestations of sepsis include those related to the systemic response to infection (tachycardia, tachypnea alterations in temperature and leukocytosis) and those related to organ-system dysfunction (cardiovascular, respiratory, renal, hepatic and hematologic abnormalities). Lipopolysaccharide (LPS) of gram-negative bacteria is considered to be the most important exogenous mediator of acute inflammatory response to septic shock. The LPS or endotoxin released from outer membrane of gram negative bacteria results in the release of cytokines and other cellular mediators including tumor nectrosis factor α (TNFα), interleukin-1 (Il-1), interleukin-6 (Il-6) and thromboxane A2. Extreme levels of these mediators are known to trigger many pathological events including fever, shock, intravascular coagulation leading to ischemia and organ failure.

Sickle cell anemia is another condition associated with ischemia. Sickle cell anemia is a classical phenotype of herediatry hemoglobinopathy with hemoglobin S instead of normal hemoglobin A. Sickle cell anemia is associated with hypoxia because of decreased oxygen tension with hemoglobin S. This condition leads to systemic hypoxic condition. The viscosity of deoxygenated blood is related to proportion of sickled red cells, capillary stasis and pain crisis.

Researchers have proposed various compounds for mining ischemic insult following reperfusion. Some, such as deferoxamine, allopurinol, catalase, and peroxidase, are reportedly capable of counteracting free radical production. Others, such as superoxide dismutase, are reportedly capable of destroying these radicals. Still others, such as vitamin E and molecules bearing thiol groups such as N-acetyl cysteine ("NAC") and reduced glutathione, are reportedly capable of neutralizing the free radicals. See, e.g., U.S. Pat. No. 5,498,427.

WO 88/05044 discloses the use of nitric oxide compounds for the prophylaxis and treatment of ischemic cell damage during perfusion, preservation, and reperfusion of organs in cases of cardioplegia or organ transplantations. The nitric oxides are preferably employed as stable free radicals in their reduced form. U.S. Pat. No. 4,877,810 discloses the use of the Trolox derivative of vitamin E, instead of superoxide dismutase ("SOD"), for preventing heart tissue damage upon reperfusion following cardiovascular surgery, including heart transplants. All these therapeutic approaches have been less than ideal in preventing ischemia/reperfusion injury. Therefore, there exists a need for better means of combating ischemia reperfusion injury to tissues and organs. There also exists a need for a better means of combatting ischemia caused by diseases and other conditions that are not associated with discreet reperfusive episodes, such as occur in organ transplants.

SUMMARY OF THE INVENTION

The present invention provides surprising effective combinations of NO donors, inhibitors of iNOS induction, and endopeptidase inhibitors for combating injury induced by ischemic conditions, and reperfusion following such ischemia. Ischemic injury, as determined by morphological examination and evaluated by certain critical cellular functions, was substantially eliminated by treatment with the combinations prior to ischemic insult. In contrast, the morphology and cellular functioning of control organs treated by only one compound of the combination declined continuously and substantially after the reperfusion of the organs.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 shows the levels of serum creatinine, urea nitrogen, lactate dehydrogenase and lipid peroxide in plasma, and antioxidant enzymes (catalase, CuZn SOD, Mn SOD and glutathione peroxidase) in kidneys, of animals subjected to 60 minutes of localized ischemia, measured at 24 and 96 hours after reperfusion. Three sets of animals are represented: (1) control animals not subjected to ischemia; (2) animals that were treated with NAC prior to the onset of ischemia; and (3) animals that were not treated with NAC before the onset of ischemia.

DETAILED DESCRIPTION OF THE INVENTION

Figure 2A:
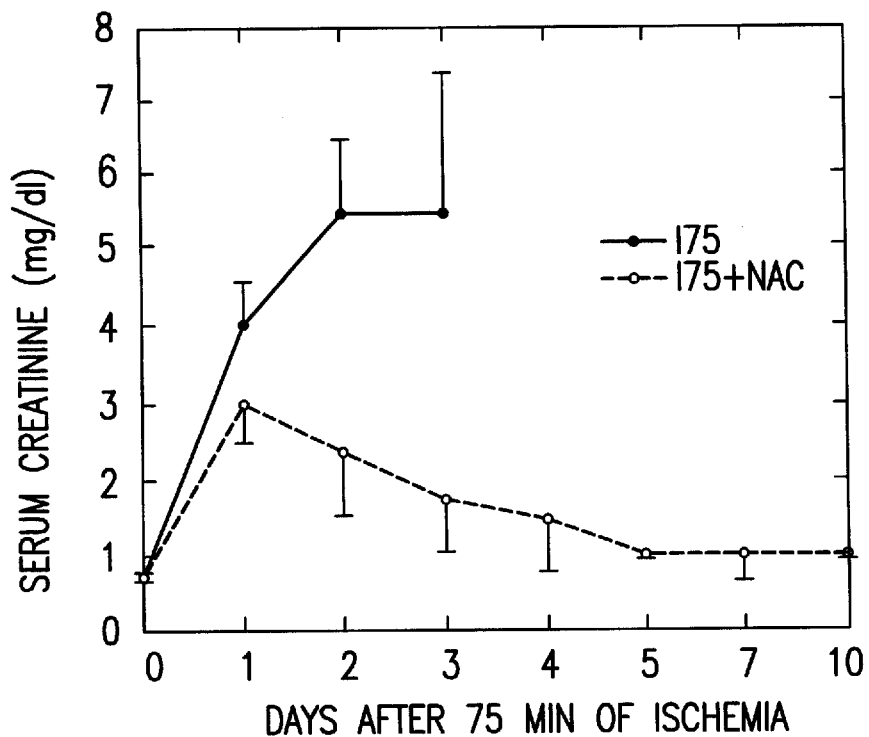
FIG. 2 shows the levels of serum creatinine and blood urea nitrogen in the blood of animals with a kidney subjected to 75 minutes of localized ischemia, measured each day for ten days after reperfusion. Two sets of animals are represented: (1) animals that were not treated with any drugs before the onset of ischemia; and (2) animals that were treated with NAC before the onset of ischemia.

Before the present compositions and methods are disclosed and described, it is to be understood that this invention is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

As used throughout this specification and the claims, the following terms have the following meanings:

"Ischemia" means a temporary or prolonged lack or reduction of oxygen supply to an organ or skeletal tissue. Ischemia can be induced when an organ is transplanted, or by conditions such as septic shock and sickle cell anemia.

"Organ" means a part of a mammalian subject composed of several tissues and adapted to perform a specific function or functions. Representative organs include, but are not limited to, the heart, kidney, liver, pancreas and brain.

"Skeletal tissue" means the substance of an organic body of a skeletal organism consisting of cells and intercellular material, including but not limited to epithelium, the connective tissues (including blood, bone and cartilage), muscle tissue, and nerve tissue.

"Ischemic insult" means damage to an organ or skeletal tissue caused by ischemia.

"Subject" means any living organism, including humans, and mammals.

"A" means one or more, depending upon the context in which it is used.

"Contacting the tissue" with a drug, when used in this application, means to bring the drug into contact with the tissue by administering the drug. Thus, for example, one can contact a tissue with a drug by parenterally injecting the drug into or near the tissue, by ingesting the drug and allowing the drug to reach the tissue through metabolic pathways, or by physically immersing the tissue in a solution containing the drug.

The invention provides a method for minimizing ischemic insult to an organ or skeletal tissue exposed to ischemia. The method includes the steps of: contacting the organ or skeletal tissue with an inhibitor of inducible nitric oxide synthase (iNOS) induction, and a nitric oxide ("NO") donor; either sequentially, simultaneously or separately. The method may optionally include the step of administering to the organ or skeletal tissue an endopeptidase inhibitor.

In another embodiment the method includes the steps of: contacting the organ or skeletal tissue with an inhibitor of iNOS induction and an endopeptidase inhibitor; either sequentially, simultaneously or separately. The method may optionally include the step of administering to the organ or skeletal tissue a NO donor.

The method minimizes the insult associated with ischemia-reperfusion and particularly prevents injury associated with the excessive presence of reactive oxygen species and down regulation of antioxidant enzymes. The method may be used when various types of surgery are carried out, including heart surgery, vessel reconstruction, and transplantation of organs. The method similarly can be utilized in acute resuscitation cases such as cardiac arrest and other conditions involving circulatory collapse. The method may also be employed upon occurrence of various types of traumas in the central nervous system, cerebral hemorrhage, stroke, sub-arachnoid hemorrhage, and intracranial vascular surgery where temporary occlusion of blood vessels occurs.

The method may also be used where ischemic conditions in, e.g., the heart, kidney, intestines, liver and skeletal tissue, are induced by shock trauma, embolisms and infarctions. The method also has therapeutic value in treating conditions that induce various levels of ischemia, such as septic shock and sickle cell anemia.

Compounds that inhibit the induction of inducible nitric oxide synthase ("inhibitors of iNOS induction") include lovastatin, mevastatin, and other compounds that can activate protein kinase A ("PKA") activity. A particularly suitable inhibitor of iNOS induction is N-acetyl-cysteine.

Some NO donors that may be employed in the invention are set forth in Holtman, J. L,. *Spin Labeling in Pharma-*

*cology* pp. 1–85 (Academic Press 1984), and WO 88/05044, the contents of each being hereby incorporated by this reference, although any compound that under physiological conditions liberates NO is suitable. A particularly suitable NO donor for practicing the invention is N-nitroso-N-acetylpencillamine ("SNAP"). Another particularly suitable NO donor for practicing the invention is sodium nitroprusside.

Suitable endopeptidase inhibitors include compounds such as phosphoramidon. Phosphoramidon is an inhibitor of Endothelin Converting Enzyme ("ECE") which, because it inhibits ECE, also blocks the natural production of potent vasoconstrictors such as endothelin-1 from big endothelin in endothelial cells. Phosphoramidon has proven especially and surprisingly effective at preventing and minimizing ischemic insult to organs and skeletal tissue when administered along with an inhibitor of iNOS induction such as N-acetyl-cysteine. The use of endopeptidase inhibitors in conjunction with both an inhibitor of iNOS induction and NO donor has proven especially effective for combating ischemic insult.

It may also be appropriate to administer further drugs that will have a positive effect on the particular indication involved via multi-factor treatment. For example, a plasma volume expander such as dextran or hydroxyethyl starch, superoxide dismutase ("SOD"), calcium blocking agents such as nifedipine, nimodipine, verapamil, lidoflazine, and flunarizine, diuretics, and antiedemics may also be administered.

The method can be used to precondition organs before they are subjected to ischemia when various types of planned surgery are carried out. For preconditioning an organ that will be subjected to ischemia and reperfusion, the dose of inhibitor of iNOS induction may preferably be in the range of from about 100 to about 300 mg./kg. body weight. The dose of NO donor may preferably range from about 1 to 2 milligrams per kilogram of body weight. The dosage may deviate from this general range depending upon the particular drug and indication involved in each case. A more preferable dosage range for the inhibitor of iNOS induction is from about 150 to 300 mg./kg., while about 300 mg./kg. body weight is especially preferred. About one mg./kg. body weight is an especially preferred dosage for the NO donor.

A preferred dosage for an endopeptidase inhibitor, when administered to combat ischemia before a planned ischemic episode, is about 3 to 20 milligrams per kilogram of body weight. A more preferred dosage range is from about 6 to about 20 milligrams per kilogram of body weight, and about 10 milligrams of endopeptidase inhibitor per kilogram of body weight is especially preferred.

The amounts and ratios of active ingredients administered in the method can, of course, vary, depending upon the particular application of the method. A particularly effective method of the present invention, especially useful for perfusion of organs or skeletal tissue prior to ischemic insult, comprises administering to a subject N-acetyl-cysteine, sodium nitroprusside, and phosphoramidon in the amounts described above. Such administration can be simultaneous, sequential, or separate.

The method can be performed in a number of different ways in accordance with the invention. Due to the nature of the active compounds, however, administration is often performed parenterally, e.g., by intraarterial, intravenous, subcutaneous, or intramuscular injection. The parenteral injection can be administered continuously or intermittently in discreet injections. As a general rule, the drugs can be administered in the form of a sterile aqueous solution buffered to a physiologically acceptable pH. The solution can be prepared well in advance of the administration or, depending upon the actual compounds employed, in direct conjunction with or just before administration.

If the method is employed as a prophylactic measure by administering the active compounds parenterally in discreet dosages prior to an ischemic episode there are certain timing protocols that have been developed to optimize the effectiveness of the method. The inhibitor of iNOS induction can preferably be administered, for example, preferably at about 1 to 8 hours, more preferably at about 1 to 4 hours, and most preferably at about three hours, prior to an ischemic episode. It may also be particularly helpful to administer the inhibitor of iNOS induction in two or more doses, the last being closer to the onset of ischemia, and particularly at about 30 minutes prior to ischemia. The inhibitor of iNOS induction may preferably be buffered to a physiologically acceptable pH which may be between about 7.4 and 7:45 and most preferably about 7.4.

The NO donor may similarly be administered before the onset of ischemia, and preferably at about 3 to 15 minutes before the onset of ischemia. In a particularly effective method, the NO donor is intravenously injected to the subject about 5 minutes before the onset of ischemia.

An endopeptidase inhibitor can be administered in discreet doses before the onset of ischemia, preferably at about 30 to 90 minutes, and more preferably at about 60 minutes prior to an ischemic episode. It may also be particularly helpful to administer the endopeptidase inhibitor in two or more doses, the last being closer to the onset of ischemia, and particularly at about 30 minutes prior to ischemia. The endopeptidase inhibitor may also be buffered to a physiologically acceptable pH which may optimally be about 7.4.

Other modes of administration can include inhalation of an aerosol, subcutaneous, and topical administration. Further administration methods can include oral administration, particularly when the active compounds are encapsulated, or rectal administration, particularly when the active compounds are in suppository form.

The active components can be administered along with a pharmaceutically acceptable carrier suitable for the selected mode of administration. A pharmaceutically acceptable carrier includes any material that does not cause significant undesirable biological effects or interact in a deleterious manner with any of the other components of the pharmaceutical composition. Various dosage forms can be employed. Actual methods of preparing such dosage forms are known or will be apparent to those skilled in the art. (See, e.g. Martin, E. W. *Remington's Pharmaceutical Sciences*, latest edition, Mack Publishing Co., Easton, Pa.)

The method may also be used during the storage or preservation of harvested organs to be implanted. In particular, the method can be carried out by storing a harvested organ in the composition of the present invention. Although the method is optimally performed by immersing the entire tissue or organ in the composition, it would also be effective by only immersing part of the organ or tissue in the composition. Preferred preservation solutions such a commercially available VIASPAN® (UW Preservation Solution) are modified by the addition of an inhibitor of NOS induction (preferably 5–30 mmol/liter), and an endopeptidase inhibitor (preferably 5–50 mmol/liter). Particularly preferred inhibitors of iNOS induction and endopeptidase inhibitors for storage solutions are, respectively, N-acetyl-cysteine and phosphoramidon. The method can also be carried out during the reperfusion of an organ or skeletal tissue that has been exposed to ischemic insult.

The present invention is more particularly described in the following examples which are intended as illustrative only because numerous modifications and variations therein will be apparent to those skilled in the art.

EXAMPLES

The following examples are put forth so as to provide those of ordinary skill in the art with a complete disclosure and description of how the methods claimed herein are performed and evaluated, and are intended to be purely exemplary of the invention and are not intended to limit the scope of what the inventor regards as his invention. Efforts have been made to ensure accuracy with respect to numbers (e.g., amounts, temperature, etc.) but some errors and deviations should be accounted for.

Protocol—Male Sprague-Dawly rats weighing 250–300 grams were anesthetized with sodium pentobarbital (50 mg per kg) injected intraperitoneally and then heparinized by injecting 0.25 milliliters of sodium heparin (1000 units per milliliter) by cannulating the inferior vena cava through the left femoral vein with silicone rubber tubing. The abdomen of each rat was opened through a mid-line incision. The left kidney was mobilize with minimum trauma and ischemia was induced in the left kidney by applying a silicone tourniquet around the entire renal pedicle. The right renal vessels were completely occluded, removed and discarded. The left kidneys from animals sham operated by a mid-line incision without the ischemia reperfusion protocol served as controls.

Example 1

Three groups of animals are represented: (1) control animals not subjected to ischemia; (2) animals that were treated with N-acetyl-cysteine (200 mg) 2 hours prior to onset of ischemia; and (3) animals that were not treated with N-acetyl-cysteine before the onset of ischemia. Ischemia was induced for 60 minutes. After the ischemia and reperfusion was completed the experimental animals and control animals were examined for kidney functions as determined by levels of creatinine and BUN (markers of kidney functions), and lactate dehydrogenase and lipid peroxide (markers of kidney tissue damage). The kidney tissues were also examined for antioxidant enzyme activity (catalase, CuZn SOD, Mn SOD and glutathione peroxidase) to measure their ability to detoxify ischemia/reperfusion-induced reactive oxygen species. A summary of the results obtained at 24 and 96 hours after reperfusion is graphically illustrated in FIG. 1.

Example 2

200 mg. of N-acetyl-cysteine was administered to a first group of animals at two hours and 30 minutes prior to ischemia. A second group was not treated with N-acetyl-cysteine prior to ischemia. Ischemia was then induced in each group for 75 minutes. Plasma creatinine and blood urea nitrogen levels were measured in each of the groups of animals periodically for 10 days following reperfusion of the organ. Results of the measurements are graphically summarized in FIG. 2. The survival rate of the animals tested in this set of experiments is summarized in FIG. 3.

Example 3

200 mg. of N-acetyl-cysteine, 5 mg. of phosphoramidon, and 2 mg. of sodium nitroprusside were administered to a first group of animals at two hours, 45 minutes, and 15 minutes, respectively, prior to ischemia. A second group was treated with 200 mg. of N-acetyl-cysteine two hours prior to ischemia. A third group was treated with 200 mg. of N-acetyl-cysteine and 2 mg. of sodium nitroprusside at two hours and 15 minutes, respectively, prior to ischemia. A fourth group of animals was not treated with any drugs. Normothermia ischemia was induced in each of groups 1–4 for 90 minutes. A fifth group of animals was not treated or exposed to ischemia. Plasma creatinine and blood urea nitrogen levels were measured in each group of animals periodically for 14 days following reperfusion as summarized in FIG. 4. The survival rate of animals in this set of experiments is summarized in FIG. 5.

Discussion of Results

Figure 2B:
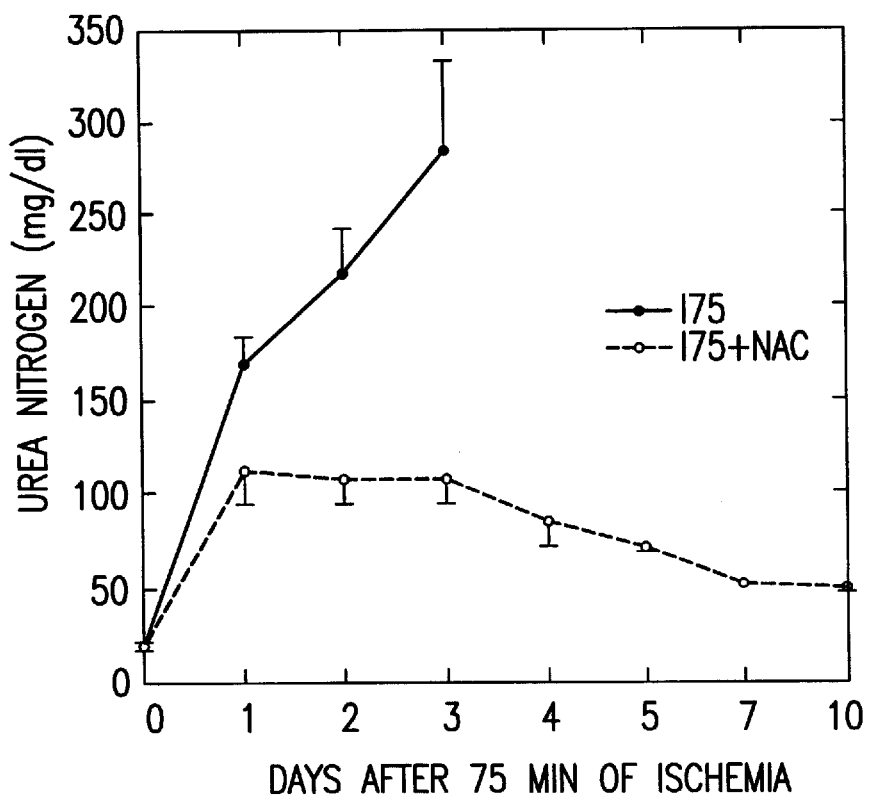

As shown in FIG. 1, N-acetyl-cysteine when given before ischemia was able to protect the kidney against tissue damage as evidenced by the relatively lower levels of creatinine and BUN and higher levels of enzyme activity of catalase CuZn SOD, Mn SOD and GPX in drug treated tissue as compared to non-treated tissue. N-acetyl-cysteine produced much better protection of the kidney as compared to untreated animals. The levels of creatinine were almost similar to the controls. The activities of antioxidant enzymes catalase CuZn SOD, Mn SOD and GPX were similarly protected better with N-acetyl-cysteine than in kidneys from untreated animals. As shown in FIG. 2, serum creatinine and urea nitrogen levels return to pre-ischemic levels when treated with N-acetyl-cysteine.

Figure 4A:
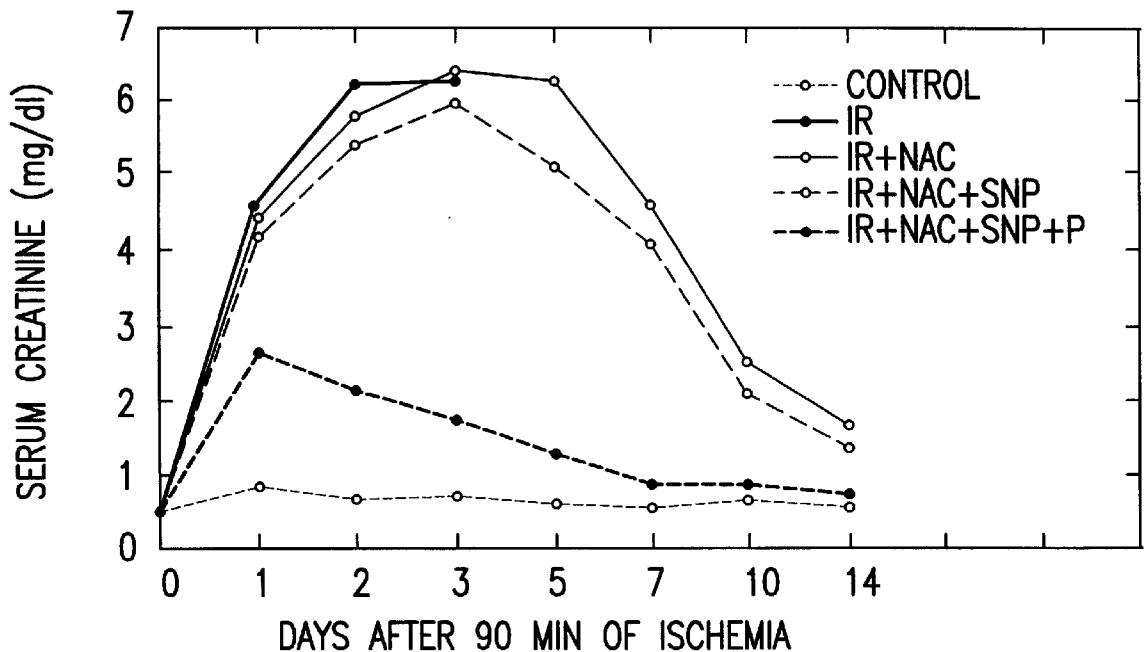
FIG. 4 shows the levels of serum creatinine and blood urea nitrogen in the blood of animals subjected to 90 minutes of localized ischemia, measured each day for fourteen days after reperfusion. Five sets of animals are represented: (1) control animals that were not subjected to ischemia; (2) animals that were not treated before the onset of ischemia; (3) animals that were treated with NAC, phosphoramidon (P), and sodium nitroprusside (SNP) before the onset of ischemia; (4) animals that were treated with NAC and sodium nitroprusside before the onset of ischemia; and (5) animals that were treated with NAC before the onset of ischemia.
Figure 4B:
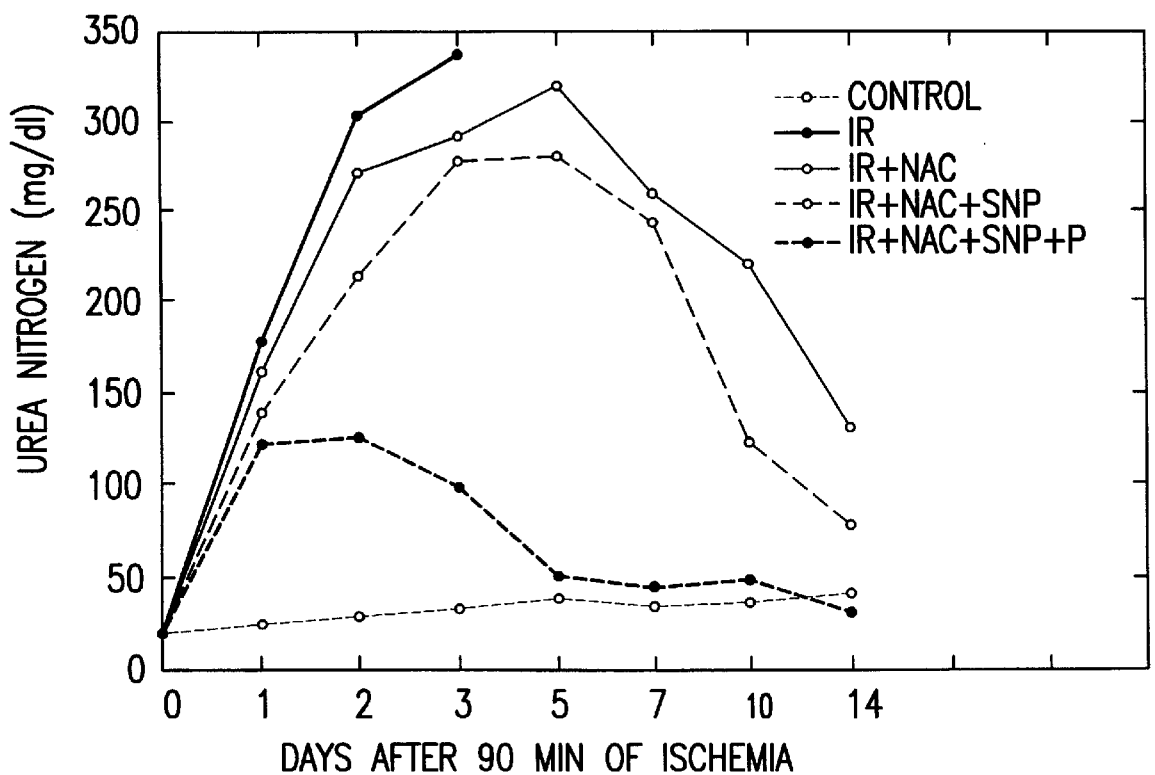

The survival rates can be partly attributed to the variations in urea nitrogen and serum creatinine levels that are shown in FIG. 4. As shown in FIG. 4, N-acetyl-cysteine, phosphoramidon and sodium nitroprusside, when administered before ischemia, were extremely effective returning the serum creatinine and BUN levels to normal in a short period of time. Indeed, 14 days after the ischemic episode, the serum creatinine and BUN levels in the kidneys of the treated animals were substantially normalized. In contrast, the serum creatinine and BUN levels of the untreated animals rose over the first few days after ischemia to unacceptable levels that eventually led to death of all the animals.

Figure 3:
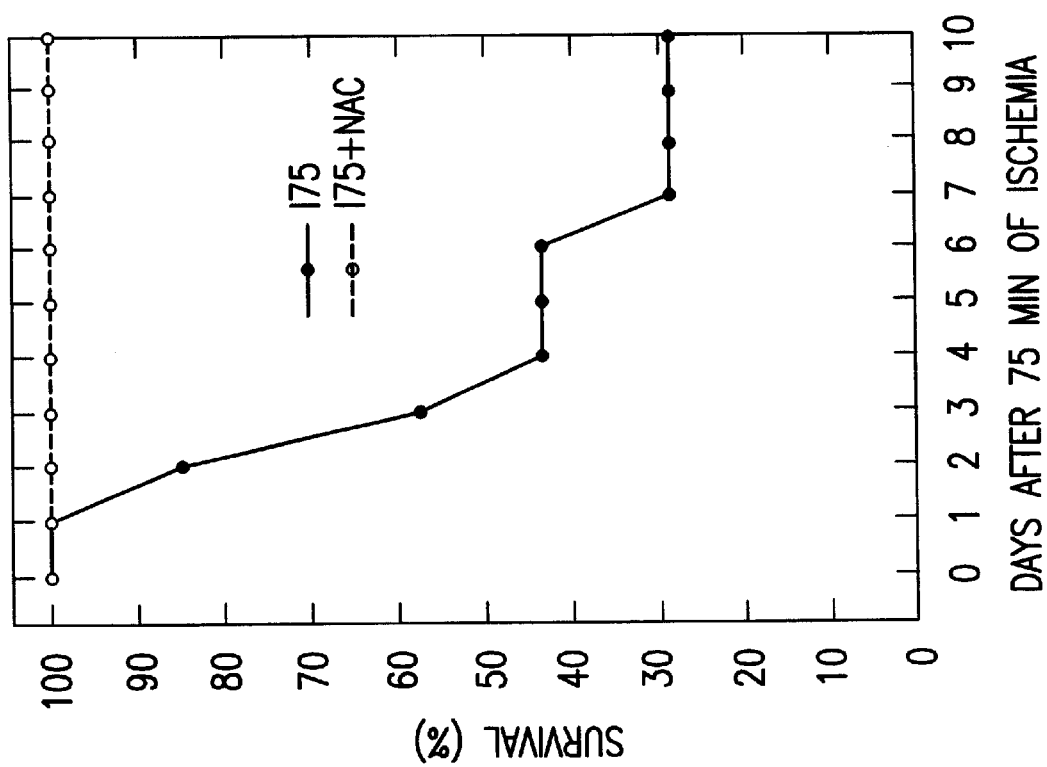
FIG. 3 shows the survival rates of animals subjected to 75 minutes of ischemia, as plotted against the days following reperfusion. The two sets of annals represented in FIG. 2 are again represented.
Figure 5:
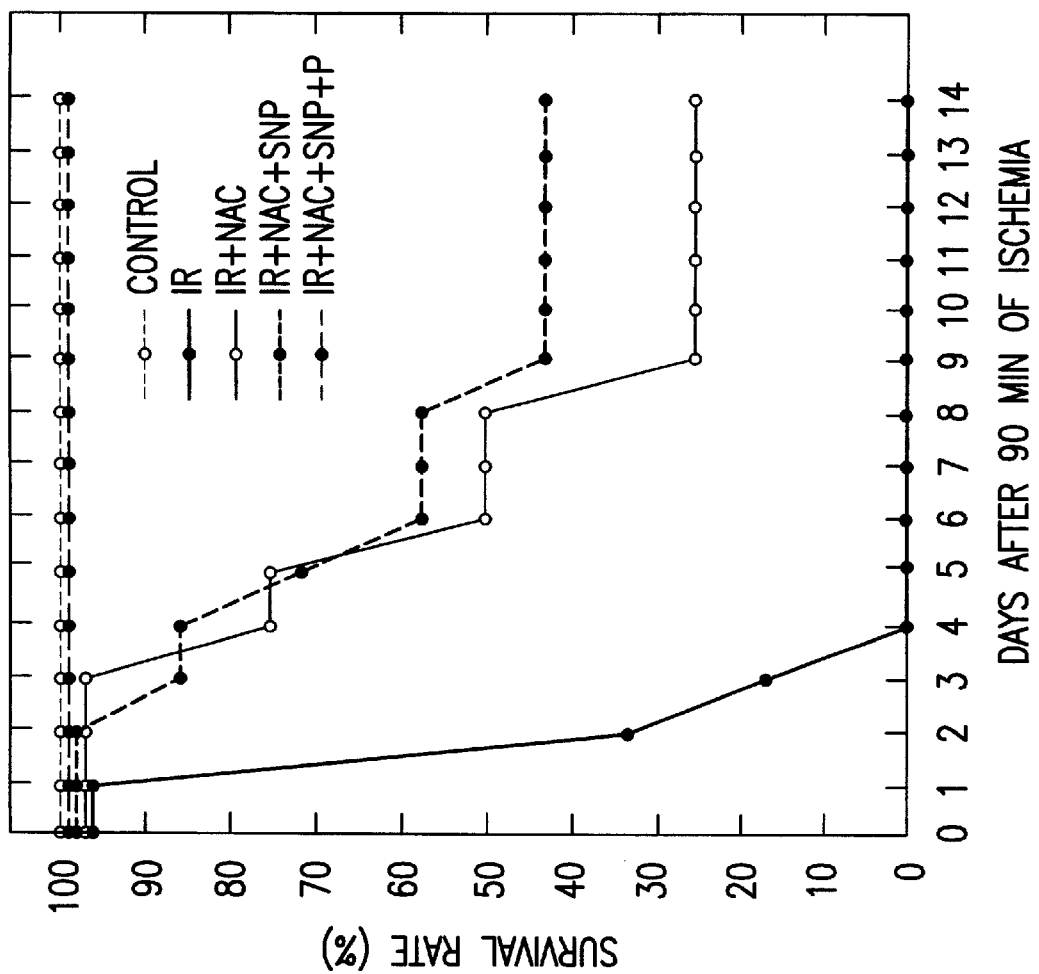
FIG. 5 shows the survival rates of animals subjected to 90 minutes of ischemia, as plotted against the days following reperfusion. The five sets of animals represented in FIG. 4 are again represented.

The reduced tissue damage in the N-acetyl-cysteine treated animals resulted in substantially improved survival rates for animals subjected to 75 minutes of ischemia, as demonstrated in FIG. 3. N-acetyl-cysteine alone was not very effective, however, after ischemic episodes of 90 minutes, as shown in FIG. 5, with less than a 30% survival rate. Sodium nitroprusside, when administered in conjunction with the N-acetyl-cysteine, substantially improved the survival rates of animals subjected to 90 minutes of ischemia. When N-acetyl-cysteine, sodium nitroprusside and phosphoramidon were administered together, however, 100% of the animals survived. (FIG. 5)

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method for minimizing ischemic insult to an organ or skeletal tissue of a subject comprising contacting the organ or tissue with an inhibitor of iNOS induction, a nitric oxide donor, and an endopeptidase inhibitor, either sequentially, simultaneously, or separately.

2. The method of claim 1 wherein the inhibitor of iNOS induction is N-acetyl-cysteine.

3. The method of claim 1 wherein the inhibitor of iNOS induction is a compound capable of activating PKA activity.

4. The method of claim 3 wherein the compound is lovastatin or mevastatin.

5. The method of claim 1 wherein the nitric oxide donor is sodium nitroprusside.

6. The method of claim 1 wherein the nitric oxide donor is N-nitroso-N-acetylpencillamine.

7. The method of claim 1 wherein the endopeptidase inhibitor is an endothelin converting enzyme inhibitor.

8. The method of claim 7 wherein the endopeptidase inhibitor is phosphoramidon.

9. The method of claim 1 wherein the inhibitor for iNOS induction is N-acetyl-cysteine, the nitric oxide donor is sodium nitroprusside, and the endopeptidase inhibitor is phosphoramidon.

10. The method of claim 1 wherein, prior to an onset of ischemia, about 150 to about 200 mg. per kg. body weight of inhibitor of INOS induction is administered to the subject.

11. The method of claim 10 wherein the inhibitor of INOS induction is N-acetyl-cysteine.

12. The method of claim 1 wherein, prior to an onset of ischemia, about 1 to about 2 mg./kg. body weight nitric oxide donor is administered to the subject.

13. The method of claim 12 wherein at from about three to about fifteen minutes prior to an onset of ischemia, about 1 to about 2 mg./kg. body weight sodium nitroprusside is administered to the subject.

14. The method of claim 1 wherein, from about 30 to about 90 minutes prior to ischemia, about 3 to about 20 mg./kg. body weight endopeptidase inhibitor is administered to the subject.

15. The method of claim 14 wherein the endopeptidase inhibitor is phosphoramidon.

16. The method of claim 1 wherein the organ or tissue is contacted with the nitric oxide donor, the inhibitor of iNOS induction and the endopeptidase inhibitor by at least partly immersing the organ or skeletal tissue in a composition comprising a nitric oxide donor, an inhibitor of iNOS induction, and an endopeptidase inhibitor.

17. The method of claim 16 wherein the nitric oxide donor is sodium nitroprusside, the inhibitor of iNOS induction is N-acetyl-cysteine, and the endopeptidase inhibitor is phosphoramidon.

18. The method of claim 9 wherein the organ or tissue is contacted with the N-acetyl-cysteine, sodium nitroprusside and phosphoramidon by intravenous administration to the subject.

19. The method of claim 18 wherein the N-acetyl-cysteine and sodium nitroprusside are administered intravenously to the subject upon reperfusion of the organ or tissue.

* * * * *